(12) United States Patent
Tabibian

(10) Patent No.: US 9,839,604 B1
(45) Date of Patent: Dec. 12, 2017

(54) COMPOSITION FOR AN ANTI-AGING TREATMENT

(71) Applicant: Parham Tabibian, MD, Inc., Los Angeles, CA (US)

(72) Inventor: Parham Michael Tabibian, Los Angeles, CA (US)

( * ) Notice: Subject to any disclaimer, the term of this patent is extended or adjusted under 35 U.S.C. 154(b) by 247 days.

(21) Appl. No.: 14/550,138

(22) Filed: Nov. 21, 2014

(51) Int. Cl.
| | | |
|---|---|---|
| *A61K 36/82* | (2006.01) |
| *A61K 36/15* | (2006.01) |
| *A61K 36/185* | (2006.01) |
| *A61K 8/97* | (2017.01) |
| *A61K 33/00* | (2006.01) |
| *A61K 36/11* | (2006.01) |
| *A61K 36/81* | (2006.01) |
| *A61K 31/566* | (2006.01) |
| *A61K 31/385* | (2006.01) |
| *A61K 31/122* | (2006.01) |
| *A61K 31/728* | (2006.01) |
| *A61K 31/197* | (2006.01) |
| *A61K 36/45* | (2006.01) |
| *A61K 31/375* | (2006.01) |
| *A61K 31/52* | (2006.01) |
| *A61K 8/49* | (2006.01) |
| *A61K 8/44* | (2006.01) |
| *A61K 8/63* | (2006.01) |
| *A61K 8/35* | (2006.01) |
| *A61K 8/11* | (2006.01) |
| *A61K 9/48* | (2006.01) |
| *A61Q 19/08* | (2006.01) |

(52) U.S. Cl.
CPC .......... *A61K 8/97* (2013.01); *A61K 8/11* (2013.01); *A61K 8/355* (2013.01); *A61K 8/44* (2013.01); *A61K 8/4953* (2013.01); *A61K 8/4973* (2013.01); *A61K 8/4986* (2013.01); *A61K 8/63* (2013.01); *A61K 9/48* (2013.01); *A61K 31/122* (2013.01); *A61K 31/197* (2013.01); *A61K 31/375* (2013.01); *A61K 31/385* (2013.01); *A61K 31/52* (2013.01); *A61K 31/566* (2013.01); *A61K 31/728* (2013.01); *A61K 33/00* (2013.01); *A61K 36/11* (2013.01); *A61K 36/15* (2013.01); *A61K 36/45* (2013.01); *A61K 36/81* (2013.01); *A61K 36/82* (2013.01); *A61Q 19/08* (2013.01)

(58) Field of Classification Search
None
See application file for complete search history.

(56) References Cited

U.S. PATENT DOCUMENTS

| 8,128,912 B2 * | 3/2012 | Canham ............... A61K 8/25 424/401 |
| 2003/0059451 A1 * | 3/2003 | De La Charriere ..... A61K 8/63 424/401 |
| 2003/0091605 A1 * | 5/2003 | Mummert ............. A61K 8/4986 424/401 |
| 2008/0014156 A1 * | 1/2008 | Horn ..................... A61K 8/11 424/59 |
| 2011/0293588 A1 * | 12/2011 | McCleary ............. A61K 31/122 424/94.1 |

\* cited by examiner

*Primary Examiner* — Chris R Tate
*Assistant Examiner* — Randall Winston
(74) *Attorney, Agent, or Firm* — Michael D. Eisenberg

(57) ABSTRACT

An anti-aging composition comprising: pinebark extract, polypodium leucotomos, ashwagandha extract, dehydroepiandrosterone, white tea extract, alpha lipoic acid, vitamin K2, bioactive silicon, hyaluronic acid, trimethylglycine, and optionally, piperine, green tea extract, folic acid, vitamin C, camu camu, and blueberry extract.

7 Claims, 1 Drawing Sheet

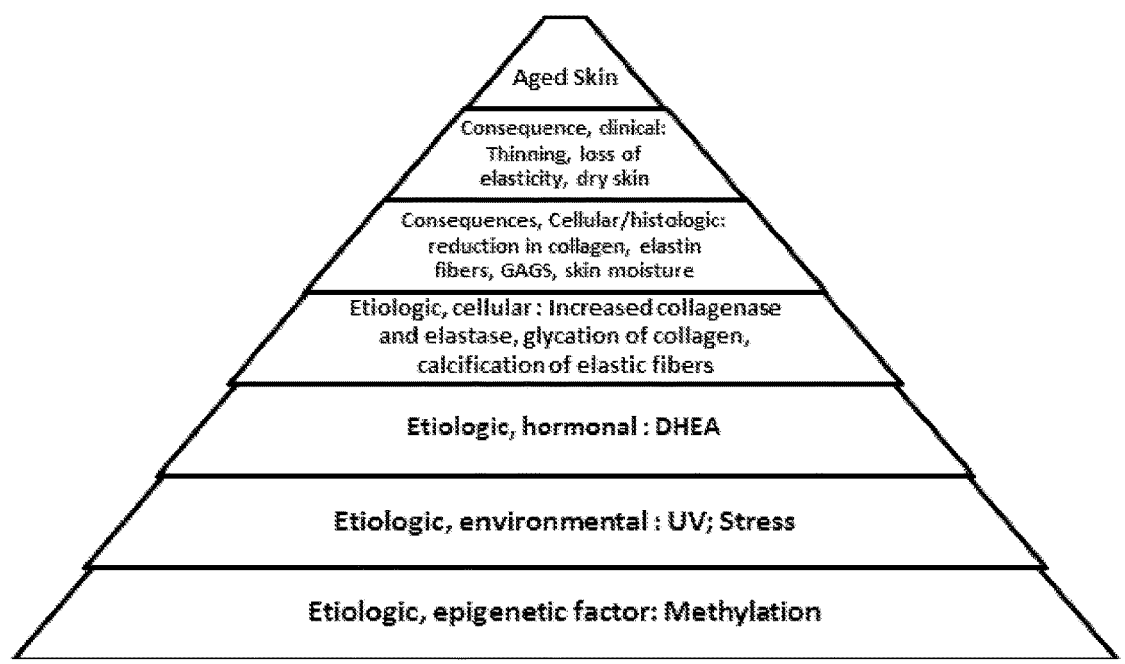

COMPOSITION FOR AN ANTI-AGING TREATMENT

TECHNICAL FIELD

The present invention, in some embodiments thereof, relates to the field of dermatology and more particularly to anti-aging products.

BACKGROUND OF THE INVENTION

Human skin, like all other organs, undergoes chronological and biological aging. In addition, unlike other organs, skin is in direct contact with the environmental factors, thus further contributing to premature aging. Age-related changes in elderly skin include clinical, histological, and biochemical changes. The clinical effects of aging on the skin are common to all humans and are characterized by wrinkles, dry and thinning skin and volume loss. Aside from the visible effects of aging, aging has a psychological impact in individuals by reducing self-esteem or even causing others to misjudge the competency of individuals.

The development of signs of skin aging has traditionally been considered as due to both intrinsic and extrinsic factors. Intrinsic factors refer to structural, biochemical, and physiological changes that occur as a natural consequence of aging and are considered genetically determined. Intrinsic aging is also called chronologic or "natural" aging. Extrinsic factors include environmental factors such as smoking, alcohol consumption, air pollution, ultraviolet exposure and stress. Of all extrinsic causes, UV radiation from sunlight has the most widespread documentation of its negative effects on the skin and thus is considered as the most important extrinsic factor as it relates to skin aging. Because of this, extrinsic aging is often referred to as photoaging.

Even without extrinsic factors such as stress or exposure to UV light, skin starts to begin the inherent process of aging around an individual's mid-twenties as the productions of collagen and elastic fibers decline. All layers of skin (epidermis, dermis, dermal connective tissue and subcutaneous fat) atrophy over time with skin, while skin becomes increasingly dehydrated to due to increased transepidermal water loss in increasingly atrophic skin. Elastin provides much of the elastic recoil properties of skin, arteries, lungs, and ligaments. Loss of elastin is a major part of what causes visible signs of aging (wrinkles, sagging) in skin. Eighty percent of the dry weight of skin is reported to be collagen, responsible for the tensile strength of skin.

Intrinsic and extrinsic factors do not operate exclusively and independently of each other. The intrinsic rate of skin aging in any individual can be dramatically influenced by environmental factors, such as with the amount of exposure to UV radiation and overall stress experienced by the individual. With increasing UV exposure as well as stress, skin's ability to repair itself is diminished.

Telomeres, repetitive and protective nucleotide regions that help prevent chromosome degradation, are known to be linked to aging, cancer, and death. These regions at the ends of chromosomes help protect genomic integrity by acting as a buffer during the inevitable degradation of the end of DNA strands during cellular division. In addition to the inevitable degradation caused during DNA replication, telomeres have been shown to be highly susceptible to damage from oxidative stress. Telomeres shorten over time and eventually the accumulated damage results in non-dividing cells, cellular senescence, and apoptosis. This molecular and cellular process produces the effects of aging: muscles weaken, eyesight and hearing fade, organs fail, and with respect to the skin, cutaneous signs of aging such as wrinkles. Counteracting the continued loss (shortening) of telomeres are enzymes called telomerase. This protein adds nucleotide repeats at to the 3' end of DNA strands, which delays the eventually effects of telomeric shortening. However, telomerase levels naturally decline with age.

UV light, whether from the sun or other sources, breaks down collagen and impairs the skin's ability to create new collagen. UV light also damages elastic fibers, cross-linked glycoproteins which are produced by fibroblasts in the extracellular matrix of skin, and which impart elasticity to skin. Similarly, stress-induced release of cortisol has been linked to collagen loss in skin. Stress also adds to the natural intrinsic loss of telomeres by directly altering telomere dynamics, causing attrition and hindering restoration of chromosomal length.

The current and traditional understanding of skin aging (i.e. extrinsic vs. intrinsic) factors is too generalized. This invention is a novel multi-tiered conceptual approach to skin aging based on DNA (genomic), environmental, hormonal, and cellular and physiologic and etiologic factors implicated and observed in aging skin. The suggested composition of the present invention has been specifically selected to address these factors.

Referencing FIG. 1, a number of etiological factors lead to consequence ultimately resulting in aged skin. The etiological factors are epigenetic, environmental, hormonal, and cellular. Methylation of DNA relates the epigenetic factor. UV light and stress are environmental factors. DHEA is a hormonal factor. These lead to consequences. The consequences include cellular and histological consequences such as reduction in collagen, elastin fibers, glycosaminoglycans (GAGs), skin moisture. Clinical cutaneous consequences include thinning, loss of elasticity, and dryness. The resulting feature of all of these factors is the appearance of aged skin.

Epigenetic factors play a vital and essential role in cutaneous aging. Epigenetics is the underpinning of the other factors. Epigenetics refers to changes in genes expression resulting without changes in the underlying DNA sequence. Unlike genetic mutations, which can take generations to result in functional changes in gene expression, epigenetic changes in gene expression can result from a single "stress" event within an individual's lifetime and can have profound consequences within a matter of days.

Epigenetic changes in gene expression occur primarily through changes in DNA methylation and chromatic structure. Methylation is the process of adding one or more methyl groups onto a nucleotide sequence. This a common signaling tool that cells use to lock genes in the "off" position and to perform DNA repair. Methylation is a biochemical process that is essential for the proper function of almost every physiologic system in the body.

Authorities consider enhancement of methylation as critical in protecting against many diseased states, including cancer, liver disease, and neurological disorders. With respect to aging, there is a global and continued loss of DNA, consistent with the notion that DNA methylation is in fact a dynamic and ongoing process. Furthermore, environmental factors appear to directly impact epigenetic mechanisms such as DNA methylation. Lending support to this notion is a longitudinal study of twin children which indicated that there was a documented divergence of methylation patterns among twin children due to environmental factors who were separated for several years from each other. Other factors that decrease methylation include smoking, alcohol consumption, high fat diets, birth control pills, and aging itself.

Given the central and critical role of methylation in chromosomal stability which underlies all physiologic activities and biochemical reactions, including the ongoing hypomethylation that appears directly related to aging, the inventor points out that DNA methylation also affects the transcription and translation of DNA and RNA encoding for vital skin structures such as collagen, elastin, and enzymes such as collagenase and elastase. For these reasons, the inventor has found an important role and need for a natural molecule that can enhance DNA methylation in the proposed anti-aging skin formulation.

Many different treatments have been suggested to decrease the signs of aging. Many current oral and topical treatments known in the prior art focus on very narrow aspects of the dermatological effects of skin aging, such as collagen and elastic fibers, UV protection, or antioxidants. Cosmetic procedures such as chemical peels, radiofrequency, or laser treatments can help to increase the production of collagen, and/or elastic fibers, but these represent a rather narrow focus of treatment. They do not address the plurality of factors, including genetic factors, clinical and environmental factors, hormonal changes, and complex cellular and physiologic changes that are implicated in and observed in skin aging. Furthermore, many of these treatments are expensive and are not options for all individuals, especially since the treatments may cause pigmentation lose that would be more obvious on darker skin tones. Similarly, injections of foreign material such as calcium hydroxylapatite and cross-linked hyaluronic acid focus solely on filling and adding volume to the deep dermal or subcutaneous tissue, and are also limited in their scope of therapy and therapeutic benefits. Such injections typically last for up to 2 years and require repeated re-injections. Finally surgical treatments such as face lifts focus on purely aesthetic considerations (tightening loosening skin) and carry their own inherent risks associated with surgical procedures.

There is a need to have a single effective composition that helps to address a plurality of factors of skin aging as described below and that does not require surgery, injections, or topical and oral preparations that merely mitigate against a narrow scope of causes of skin aging.

The present invention is unique in several respects. It is the only product ever formulated based on a novel multi-tiered understanding that reflects both etiologic factors as well as end-result changes (consequences) observed histologically in the tissue of aged skin. The composition recognizes and highlights the basic and vital role of epigenetics, specifically DNA methylation, in skin aging. As such, it is the only known formulation geared towards ameliorating signs of skin aging that specifically incorporates folic acid and trimethyglycine as potent DNA methylators. Next the formulation addresses the vital role of environmental factors such as stress which can in turn also affect how our DNA methylates. Once the different etiologic factors (genomic, clinical, hormonal, and cellular) are addressed, the formulation addresses the observed cellular and histologic changes in skin. The final end result or goal of this composition addresses all of the necessary underlying etiologic and physiologic/cellular observed changes. To that end 14 natural molecules that work synergistically together to address all the factors described above have been included.

Given the interdependency of the factors listed above, as well as the mechanisms of actions of the fourteen molecules, there is no need for any one component to be maximally dosed in order to achieve its limited scope of benefits. For instance, rather than using the maximal or high doses of Vitamin C (as found in Camu Camu) to increase collagen synthesis, collagenase inhibitor white tea extract is included in order to reduce the ongoing loss of collagen by this enzyme. Thus, lower doses of Vitamin C can be included for this specific purpose. Furthermore, given the invariably interlocked mechanisms of cellular aging addressed in the formulation, improvement in one factor (such as healthier elastic fibers) can have a corresponding positive impact on another factor (less overall elastase released by the body).

BRIEF SUMMARY OF EMBODIMENTS OF THE INVENTION

The present invention is represented by a comprehensive unique formulation. In an embodiment of formulation there is a combination of fourteen natural ingredients that work synergistically through their physiologic mechanisms to address ten 10 different factors that are hereby identified as being critical in cutaneous aging. The composition of the present invention is configured for oral use.

While many current treatments known in the prior art focus on very narrow aspects of the dermatological effects of aging none are able to treatment all of the factors. Some of the current solutions require invasive surgery or expensive injections that require annual upkeep. Some solutions include topical application of substances that cannot be absorbed through the skin such as collagen or elastin. There is a need to have a single effective composition to help treat a plurality of above factors of aging that does not require surgery or injections.

The present invention relates to a composition for an anti-aging treatment. The composition comprising: pinebark extract; polypodium leucotomos; ashwagandha extract; dehydroepiandrosterone; white tea extract; alpha lipoic acid; vitamin K2; bioactive silicon; hyaluronic acid; and trimethylglycine.

In a variant the composition includes about 50-150 mg of pinebark extract; about 120-240 mg of polypodium leucotomos; about 100-800 mg of ashwagandha extract; about 10-100 mg of dehydroepiandrosterone; about 100-1000 mg of white tea extract; about 50-1200 mg of alpha lipoic acid; about 90 to 120 mcg of vitamin K2; about 2-10 mg of bioactive silicon; about 25-100 mg of hyaluronic acid; and about 500-1500 mg of trimethylglycine.

In a variant the composition includes about about 50 mg of pinebark extract; about 120 mg polypodium leucotomos; about 100 mg of ashwagandha extract; about 10 mg of dehydroepiandrosterone; about 100 mg of white tea extract; about 50 mg of alpha lipoic acid; about 100 mcg of vitamin K2; about 5 mg of bioactive silicon; about 25 mg of hyaluronic acid; and about 500 mg of trimethylglycine.

In a variant the composition additionally includes about at least one of about 2.5-10 mg of piperine; about 100-500 mg of green tea extract; about 50-1000 mg of blueberry extract; at least one of about 100-500 mg of Camu Camu and 60-2000 mg of vitamin C; and about 0.4-5 mg of folic acid.

According to an aspect of some embodiments the composition with or without additionally inclusions is configured as a capsule containing any variation of the composition. According to an aspect of some embodiments the composition there is a method for treating aging skin, comprising ingestion of a capsule comprising any variant of the composition.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following FIGURES. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the FIGURES included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 1 is a visual depicting a number of etiological factors lead to consequence ultimately resulting in aged skin.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

An aspect of some variants of the present invention relates to a composition for treatment the dermatological effects of aging configured to for oral intake.

The composition of an embodiment of the present invention includes: pinebark extract, polypodium leucotomos, ashwagandha extract, dehydroepiandrosterone, white tea extract, alpha lipoic acid, vitamin K2, bioactive silicon, hyaluronic acid, trimethylglycine. Embodiments may vary and further include: piperine, green tea extract, folic acid, vitamin C, camu camu, and blueberry extract. These all come from natural sources.

With respect to the most fundamental factor in skin aging, DNA methylation, the present composition has incorporated the molecule trimethylglycine (TMG) and folic acid. The process of methylation involves S-adenosylmethionine, also known as SAMe. SAMe is produced in every living cell and is the most active of all methyl donors. SAMe in turn is produced upon the conversion of the amino acid methionine. When SAMe molecule passes its methyl group to DNA, it is then broken down to form homocysteine, a toxic molecule associated with widespread systemic inflammation. To prevent accumulation of homocysteine in the body, the body needs the assistance of methylation enhancing agents. Both folate and TMG (the latter extracted from sugar beets) are vital methylation enhancers, with TMG being considered to be the most effective and potent methylation enhancing agent ever known. Both TMG and folic acid are involved in reactions that cause remethylation of homocysteine back to methionine (or glutathione, which is an important antioxidant). The composition of the present invention may include 500-1500 mg of trimethyglycine. In a non-limiting example, the composition of the present invention includes about 500 mg. With respect to folic acid, the composition of the present invention may include 0.4-5 mg of folic acid. In a non-limiting example, the composition of the present invention includes about 0.4 mg.

Polypodium leucotomos comes from a fern plant, possesses antioxidant properties, and has been used in treating and preventing sunburn, eczema (atopic dermatitis), psoriasis, vitiligo, and skin cancer. Polypodium leucotomus is included in this formulation to address the deleterious impact of UV radiation. The composition of the present invention may include 120-240 mg of polypodium leucotomos. In a non-limiting example, the composition of the present invention includes about 120 mg.

Pine bark extract comes from a French maritime pine known as *Pinus pinaster*, but may also come from other sources such as peanut skin or grape seed. Pine bark extract is included in this formulation to address both the deleterious impact of UV radiation as well as the observed loss of collagen and elastic fibers. The composition of the present invention may include 50-150 mg of pinebark extract. In a non-limiting example, the composition of the present invention includes about 50 mg.

Green tea extract is an herbal derivative from green tea leaves that includes four active antioxidants: namely, epicatechin (EC), epigallocatechin (EGC), epicatechingallate (ECG), and epigallocatechin gallate (EGCG). Green tea extract is included in this formulation to address primarily the deleterious impact of UV radiation. The composition of the present invention may include 100-500 mg of green tea extract. In a non-limiting example, the composition of the present invention includes about 100 mg.

Vitamin C, also known as ascorbic acid, is the primary water-soluble, non-enzymatic antioxidant in plasma and tissues. Vitamin C is a potent reducing agent, meaning that it readily donates electrons to recipient molecules. Unlike most mammals and other animals, humans do not have the ability to make ascorbic acid and must obtain vitamin C from the diet. With aging, there is a decline in vitamin C content in both the epidermis and dermis. Excessive exposures to UV light or pollutants (e.g., cigarette smoke and ozone) appear to further lower levels of vitamin C content, primarily in the epidermis. Vitamin C plays a critical role in the maintenance of a normal mature collagen network in humans by preventing the auto-inactivation of lysyl and prolyl hyroxylase, two key enzymes in collagen biosynthesis. The antioxidant activity of vitamin C protects against UV-induced damage caused by free radicals. Camu Camu extract (a close relative of the Guavaberry or Rumberry found at the Amazonian lowlands and also known as (*Myrciaria dubia*) is incorporated into this formulation for its extraordinary high concentration of Vitamin C (ascorbic acid) measured at 2.1-3.0 grams per 100 grams. The composition of the present invention may include 100-500 mg of Camu Camu. In a non-limiting example, the composition of the present invention includes about 100 mg. Optionally, if Camu Camu is not used, Ascorbic acid as source of Vitamin C and will be incorporated in the formulation. The composition of the present invention may include 60-2000 mg of Vitamin C. In a non-limiting example, the composition of the present invention includes about 100 mg of Vitamin C.

Blueberry is a small, blue-purple fruit that belong to the genus *vaccinium*, which also includes cranberries and bilberries and is known to contain high levels of antioxidants known as anthocyanins. Blueberry extract is included in the composition as it helps slow down the process of advanced glycation end-products (AGE) formation, thus helping to prevent collagen and elastin fibers from becoming rigid, stabilizing the collagen matrix, and promoting collagen biosynthesis. The composition of the present invention may include 50-1000 mg of wild blueberry extract. In a non-limiting example, the composition of the present invention includes about 50 mg.

Stress can be defined as a physical, chemical, or emotional factor that causes bodily or mental tension and may be a factor in disease causation, and/or a state resulting from a stress. This formulation recognizes the role of stress in general in cutaneous aging and the importance of incorporating a natural molecule such as Ashwagandha (*Withania somnifera*) that can protect against some of the adverse physiologic consequences of stress.

Ashwagandha extract comes from a plant of the same name and is an adaptogen that helps to promote homeostasis. Ashwagandha has powerful antioxidant properties that seek and destroy the free radicals that have been implicated in aging and numerous disease states. The composition of the present invention may include 100-800 mg of ashwagandha extract. In a non-limiting example, the composition of the present invention includes about 100 mg.

Dehydroepiandrosterone (DHEA) is a hormone naturally produced by the body's adrenal gland and supplements can found from sources such as wild yam and soy. DHEA is the most naturally occurring hormone in the human body and is the precursor for manufacturing of other hormones including testosterone, estrogen, and progesterone. DHEA functions as a precursor to male and female sex hormones and natural levels decline with age. Levels of DHEA rise before puberty, and reach their highest levels during young adulthood. From then on, levels of DHEA decline at a rate of about 2% per year. With respect to skin, there is growing evidence that DHEA could exert an anti-aging effect through stimulation of collagen biosynthesis while improving structural organization of the dermis. The composition of the present invention may include 10-100 mg of DHEA. In a non-limiting example, the composition of the present invention includes about 10 mg.

Collagenase and elastase are proteinase enzymes that break down collagen and elastin. Elastase is a proteolytic enzyme involved in the degradation of the extracellular matrix (ECM) which includes elastin. Collagenases are a type of metalloproteinase that can cleave molecules in the ECM that includes elastin, fibronectin, laminin, and collagen. Elastase is normally utilized in the skin to degrade proteins that are, for example, within the ECM after wounding in order to eliminate this proteinaceous material by phagocytosis to permit repair. However, natural materials with anti-elastase and anti-collagenase properties can help prevent the undesirable age-associated destruction of elastin and collagen through the actions of collagenase and elastase. White tea extract is incorporated in the formulation in order to inhibit these proteinases. The composition of the present invention may include 100-1000 mg of white tea extract. In a non-limiting example, the composition of the present invention includes about 100 mg.

Alpha lipoic acid is an organosulfur compound derived from octanoic acid and is both fat and water soluble. Typically alpha lipoic acid aids in the cellular metabolism of glucose and thus also helps to prevent the glycation of collagen. Alpha lipoic acid also helps to regenerate Vitamin C for further use after eradicating free radicals. The composition of the present invention may include 50-1200 mg per day of alpha lipoic acid. In a non-limiting example, the composition of the present invention includes about 50 mg.

Vitamin K2 is the name of a group of related compounds that all contain a quinone ring but that differ in the length and degree of saturation of the carbon tail and the number of side chains. Vitamin K2 is necessary for the activation of Matrix γ-carboxyglutamic acid protein, which inhibits calcium from depositing in elastin fibers. In particular, the MK-7 form of vitamin K2 remains in the bloodstream longer and reaches levels seven- to eight-fold higher than other forms of Vitamin K1 and K2. The composition of the present invention may include 90 to 120 mcg of vitamin K2. In a non-limiting example, the composition of the present invention includes about 100 mcg of Vitamin K2, MK-7.

Bioactive silicon is a form of the chemical element silicon that has introduced nanoporous holes in its microstructure. Bioactive silicon is important for optimal collagen synthesis, and crucial for activating the hydroxylation enzymes involved in cross-linking of collagen, which improves the strength of collagen fibers. The composition of the present invention may include 2-10 mg of bioactive silicon. In a non-limiting example, the composition of the present invention includes about 5 mg.

Hyaluronic acid, is naturally present in the human body as a polysaccharide and can be extracted from rooster combs or made by bacteria in the laboratory. As we age, the percentage of hyaluronic acid in the skin decreases which also accounts for the loss of hydration and moisture in the skin. At normal levels hyaluronic acid is a major component of skin where it is involved in tissue repair. However, importantly, hyaluronic acid is also a powerful humectant that can attract and bind up to 1800 times its own weight in water, and thus helps provide moisture to dry aging skin. The composition of the present invention may include 25-100 mg of hyaluronic acid. In a non-limiting example, the composition of the present invention includes about 25 mg.

Piperine is an extract from the *piper nigrum* plant and is used to enhance the bio-absorption of the composition and allow for a lower dosage of other ingredients. The composition of the present invention may include 2.5-10 mg of piperine. In a non-limiting example, the composition of the present invention includes about 4 mg.

The composition of the present invention, therefore, addresses a plurality of factors leading to aging skin, based on a newly proposed understanding of aging skin as described above. For summary of the constituents of the composition and their intended targeting factor, see table 1.

TABLE 1

| Etiologic factor or histologic changes: | Corresponding molecule(s) addressing factors or changes: |
|---|---|
| Epigenetic Etiologic Factor: Methylation | Trimethylglycine, folic acid |
| Environmental Etiologic Factor: Stress | Ashwagandha extract |
| Environmental Etiologic Factor: UV light | Polypodium leucotomus, Pinebark extract, Green Tea, Ascorbic Acid |
| Hormonal Etiologic Factor: DHEA | DHEA |

TABLE 1-continued

| Etiologic factor or histologic changes: | Corresponding molecule(s) addressing factors or changes: |
|---|---|
| Cellular Etiologic Factor: Collagenase and Elastase | White tea extract |
| Cellular Etiologic Factor: Glycation of collagen fibers | Alpha lipoic acid, blueberry extract |
| Cellular Etiologic Factor: Calcification of elastic fibers | Vitamin K2 |
| Observed Histologic change: Reduction in collagen and elastic fibers | Ascorbic acid, Pinebark extract, Blueberry extract |
| Observed Histologic change: reduction in connective tissue (GAGs) | Bioactive Silicon |
| Observed Histologic change: reduction in skin moisture | Hyaluronic acid |

The present invention is configured to be taken orally in a capsule form. The present invention may be used either alone or in conjunction with other treatments.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

While various embodiments of the present invention have been described above, it should be understood that they have been presented by way of example only, and not of limitation. The invention is not restricted to the examples described, and the desired features can be implemented using a variety of alternative variants. Indeed, it will be apparent to one of skill in the art how alternative configurations can be implemented to implement the desired features of the present invention.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A composition for treating aging skin comprising:
   about 50-150 mg of pinebark extract;
   about 120-240 mg of polypodium leucotomos;
   about 100-800 mg of ashwagandha extract;
   about 10-100 mg of dehydroepiandrosterone;
   about 100-1000 mg of white tea extract;
   about 50-1200 mg of alpha lipoic acid;
   about 90-120 mcg of vitamin K2;
   about 2-10 mg of bioactive silicon;
   about 25-100 mg of hyaluronic acid; and
   about 500-1500 mg of trimethylglycine.

2. The composition of claim 1, comprising:
   about 50 mg of pinebark extract;
   about 120 mg polypodium leucotomos;
   about 100 mg of ashwagandha extract;
   about 10 mg of dehydroepiandrosterone;
   about 100 mg of white tea extract;
   about 50 mg of alpha lipoic acid;
   about 100 mcg of vitamin K2;
   about 5 mg of bioactive silicon;
   about 25 mg of hyaluronic acid; and
   about 500 mg of trimethylglycine.

3. The composition of claim 1 further comprising at least one of
   about 2.5-10 mg of piperine;
   about 100-500 mg of green tea extract;
   about 50-1000 mg of blueberry extract;

at least one of about 100-500 mg of Camu Camu and 60-2000 mg of vitamin C; and about 0.4-5 mg of folic acid.

4. A capsule, containing the composition of claim 1.

5. A method for treating aging skin in a subject in need thereof comprising administering to the subject an effective amount of the composition of claim 1.

6. A capsule, containing the composition of claim 3.

7. A method for treating aging skin in a subject in need thereof comprising administering to the subject an effective amount of the composition of claim 3.

* * * * *